United States Patent
Do et al.

(10) Patent No.: US 10,011,624 B2
(45) Date of Patent: Jul. 3, 2018

(54) TRANSITION METAL COMPOUND HAVING HETEROATOM, CATALYST COMPOSITION INCLUDING THE SAME AND PREPARATION METHOD OF POLYMER USING THE CATALYST COMPOSITION

(71) Applicant: LG CHEM, LTD., Seoul (KR)

(72) Inventors: Young Shil Do, Daejeon (KR); Jin Sam Gong, Daejeon (KR); Yun Jin Lee, Daejeon (KR); Choong Hoon Lee, Daejeon (KR); Seung Hwan Jung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/327,572

(22) PCT Filed: Dec. 24, 2015

(86) PCT No.: PCT/KR2015/014284
§ 371 (c)(1),
(2) Date: Jan. 19, 2017

(87) PCT Pub. No.: WO2016/105170
PCT Pub. Date: Jun. 30, 2016

(65) Prior Publication Data
US 2017/0183370 A1 Jun. 29, 2017

(30) Foreign Application Priority Data

Dec. 24, 2014 (KR) .................. 10-2014-0187785
Oct. 2, 2015 (KR) .................. 10-2015-0139075

(51) Int. Cl.
| | | |
|---|---|---|
| C07F 17/00 | (2006.01) | |
| C08F 4/6592 | (2006.01) | |
| C08F 10/00 | (2006.01) | |
| C08F 210/16 | (2006.01) | |
| B01J 31/38 | (2006.01) | |
| C07F 7/28 | (2006.01) | |
| C08F 4/659 | (2006.01) | |

(52) U.S. Cl.
CPC ............. *C07F 17/00* (2013.01); *B01J 31/38* (2013.01); *C07F 7/28* (2013.01); *C08F 4/6592* (2013.01); *C08F 210/16* (2013.01); *C08F 4/65908* (2013.01); *C08F 4/65912* (2013.01)

(58) Field of Classification Search
CPC .... C07F 17/00; C08F 4/6592; C08F 4/65908; C08F 4/65912; C08F 10/00
See application file for complete search history.

(56) References Cited

U.S. PATENT DOCUMENTS

| | | |
|---|---|---|
| 5,064,802 A | 11/1991 | Stevens et al. |
| 5,073,171 A | 12/1991 | Eaton |
| 5,703,187 A | 12/1997 | Timmers |
| 6,013,819 A | 1/2000 | Stevens et al. |
| 6,548,686 B2 | 4/2003 | Nabika et al. |
| 7,928,256 B2 | 4/2011 | Lee et al. |
| 2002/0128403 A1 | 9/2002 | Stevens et al. |
| 2004/0242880 A1 | 2/2004 | Mihan et al. |
| 2007/0225158 A1 | 9/2007 | Lee et al. |
| 2011/0152529 A1 | 6/2011 | Lee et al. |
| 2011/0160413 A1 | 6/2011 | Lee et al. |
| 2013/0203949 A1 | 8/2013 | Lee et al. |
| 2013/0211020 A1 | 8/2013 | Lee et al. |
| 2013/0211021 A1 | 8/2013 | Lee et al. |
| 2013/0211023 A1 | 8/2013 | Lee |
| 2013/0211024 A1 | 8/2013 | Lee et al. |
| 2015/0011770 A1 | 1/2015 | Lee et al. |
| 2015/0239916 A1* | 8/2015 | Do ............................ C07F 7/28 526/170 |
| 2015/0361196 A1* | 12/2015 | Do .......................... C08F 10/00 526/170 |
| 2016/0222144 A1* | 8/2016 | Kum ................... C08L 23/0815 |

FOREIGN PATENT DOCUMENTS

| | | |
|---|---|---|
| EP | 0 414 848 B1 | 10/1995 |
| EP | 0 416 815 B1 | 8/1997 |
| KR | 10-2004-0035789 A | 4/2004 |
| KR | 10-0986301 B1 | 10/2010 |

OTHER PUBLICATIONS

Bergman et al, "Synthesis and Reactions of Some 3-(2-Haloacyl)Indoles", Tetrahedron, vol. 29, 1973, pp. 971-976.
Casey et al., "[1,3]—Metal Shifts in Rhenium Alkynyl Carbene Complexes", Organometallics, vol. 20, No. 13,Jun. 25, 2001, pp. 2651-2653.
Chen et al., "A Novel Phenolate "Constrained Geometry" Catalyst System. Efficient Synthesis, Structural Characterization, and α—Olefin Polymerization Catalysis", Organometallics, vol. 16, No. 26, 1997, pp. 5958-5963.
Christie et al., "Novel Routes to Bidentate Cyclopentadienyl-Alkoxide Complexes of Titanium: Synthesis of ($\eta^5$-σ-$C_5R^1_4CHR^2CH_2CR^3R^4O$)$TiCl_2$", Organometallics, vol. 18, 1999, pp. 348-359.
Gibson et al., "Advances in Non-Metallocene Olefin Polymerization Catalysis", Chemical Reviews, vol. 103, No. 1, 2003, pp. 283-315.
Gielens et al., "Titanium Hydrocarbyl Complexes with a Linked Cyclopentadienyl-Alkoxide Ancillary Ligand; Participation of the Ligand in an Unusual Activation of a (Trimethylsilyl)methyl Group", Organometallics, vol. 17, 1998, pp. 1652-1654.

(Continued)

*Primary Examiner* — Caixia Lu
(74) *Attorney, Agent, or Firm* — Birch, Stewart, Kolasch & Birch, LLP

(57) ABSTRACT

The present invention discloses a transition metal compound including a heteroatom and having a novel structure, a catalyst composition including the same, and a preparation method of a polymer using the catalyst composition. The transition metal compound according to an embodiment of the present invention may be used as a catalyst having good copolymerization properties, and a polymer having a high molecular weight at a low density region may be prepared.

13 Claims, 2 Drawing Sheets

(56) References Cited

OTHER PUBLICATIONS

International Search Report issued in PCT/KR2015/014284 (PCT/ISA/210), dated Apr. 8, 2016.
Park et al., "Preparation of half-metallocenes of thiophene-fused and tetrahydroquinoline-linked cyclopentadienyl ligands for ethylene/α—olefin copolymerization", Dalton Transactions, vol. 39, 2010, pp. 9994-10002.
Rau et al., "Synthesis and application in high-pressure polymerization of a titanium complex with a linked cyclopentadienyl-phenoxide ligand", Journal of Organometallic Chemistry, vol. 608, 2000, pp. 71-75.
Turner et al., "Facile resolution of constrained geometry indenyl-phenoxide ligation", Chemical Communications, 2003, pp. 1034-1035.
Zhang et al., "Constrained Geometry Tetramethylcyclopentadienyl-phenoxytitanium Dichlorides: Template Synthesis, Structures, and Catalytic Properties for Ethylene Polymerization", Organometallics, vol. 23, 2004, pp. 540-546.

\* cited by examiner

TRANSITION METAL COMPOUND HAVING HETEROATOM, CATALYST COMPOSITION INCLUDING THE SAME AND PREPARATION METHOD OF POLYMER USING THE CATALYST COMPOSITION

CROSS-REFERENCE TO RELATED APPLICATIONS

This application claims the benefits of priority based on Korean Patent Application Nos. 10-2014-0187785, filed on Dec. 24, 2014, and 10-2015-0139075, filed on Oct. 2, 2015, and the entire contents of which are hereby incorporated by reference.

TECHNICAL FIELD

Technical Field

The present invention relates to a transition metal compound having a heteroatom and a novel structure, a catalyst composition including the same and a preparation method of a polymer using the catalyst composition.

Background Art

[Me$_2$Si(Me$_4$C$_5$)NtBu]TiCl$_2$ (Constrained-Geometry Catalyst, hereinafter, will be abbreviated as CGC) was reported by Dow Co. in the early 1990s (U.S. Pat. No. 5,064,802), and excellent aspects of the CGC in the copolymerization reaction of ethylene and alpha-olefin may be summarized in the following two points when compared to commonly known metallocene catalysts: (1) at a high polymerization temperature, high activity is shown and a polymer having high molecular weight is produced, and (2) the copolymerization degree of alpha-olefin having large steric hindrance such as 1-hexene and 1-octene is excellent. In addition, as various properties of the CGC during performing a polymerization reaction are gradually known, efforts of synthesizing the derivatives thereof and using as a polymerization catalyst has been actively conducted in academy and industry.

As one approach, the synthesis of a metal compound introducing various bridges instead of a silicon bridge and a nitrogen substituent and the polymerization thereof has been conducted. Typical metal compounds known until now are illustrated as the following Compounds (1) to (4) (Chem. Rev. 2003, 103, 283).

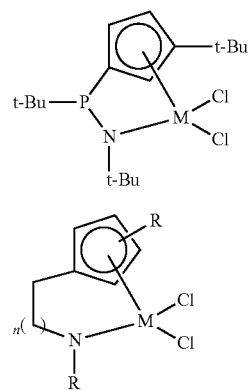

(1)

(2)

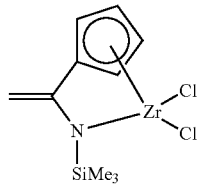

(3)

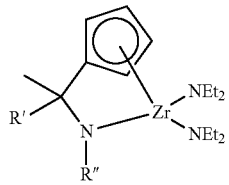

(4)

The above Compounds (1) to (4) introduce a phosphorous bridge (1), an ethylene or propylene bridge (2), a methylidene bridge (3) or a methylene bridge (4) instead of the silicon bridge of a CGC structure. However, improved results on activity, copolymerization performance, etc. could not be obtained by applying an ethylene polymerization or a copolymerization with alpha-olefin when compared to those obtained by applying the CGC.

In addition, as another approach, a compound composed of an oxido ligand instead of the amido ligand of the CGC has been synthesized, and an attempt on the polymerization using thereof has been conducted to some extent. Examples thereof are summarized in the following.

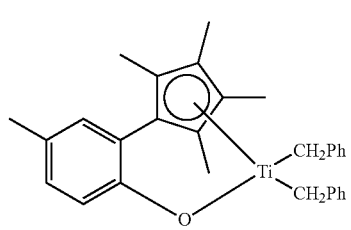

(5)

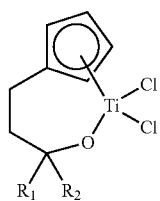

(6)

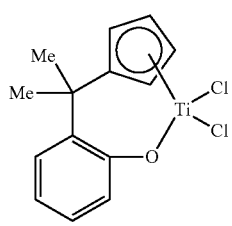

(7)

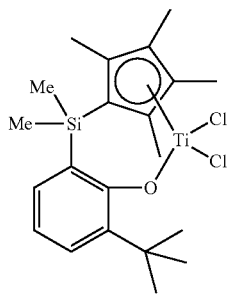

Compound (5) has been reported by T. J. Marks et al. and is characterized in that a cyclopentadiene (Cp) derivative and an oxido ligand are bridged via an ortho-phenylene group (Organometallics 1997, 16, 5958). A compound having the same bridged group and a polymerization using thereof have been reported by Mu et al. (Organometallics 2004, 23, 540). In addition, the bridging of an indenyl ligand and an oxido ligand by the same ortho-phenylene group has been reported by Rothwell et al. (Chem. Commun. 2003, 1034). Compound (6) has been reported by Whitby et al. and is characterized in that a cyclopentadienyl ligand and an oxido ligand are bridged by three carbon atoms (Organometallics 1999, 18, 348). The above catalysts have been reported to show activity in a syndiotactic polystyrene polymerization. Similar compounds have been also reported by Hessen et al. (Organometallics 1998, 17, 1652). Compound (7) has been reported by Rau et al. and is characterized in showing activity in an ethylene polymerization and an ethylene/1-hexene copolymerization at a high temperature and high pressure (210° C., 150 MPa) (J. Organomet. Chem. 2000, 608, 71). In addition, the synthesis of a catalyst (8) having similar structure as that of Compound (7) and a polymerization using the same at a high temperature and a high pressure have been filed by Sumitomo Co. (U.S. Pat. No. 6,548,686). However, not many catalysts among the above attempts are practically applied in commercial plants. Accordingly, a catalyst showing further improved polymerization performance is required, and a simple preparation method of the catalyst is required.

DISCLOSURE OF THE INVENTION

Technical Problem

According to an aspect of the present invention, a transition metal compound including a heteroatom and having a novel structure is provided.

According to another aspect of the present invention, a catalyst composition including the transition metal compound is provided.

According to further another aspect of the present invention, a preparation method of a polymer using the transition metal compound is provided.

Technical Solution

According to an aspect of the present invention, there is provided a transition metal compound represented by the following Formula 1.

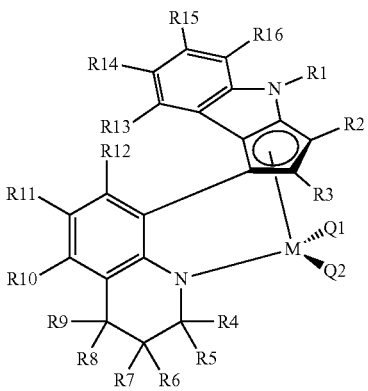

[Formula 1]

in the above Formula 1,

M is a transition metal in group 4,

Q1 and Q2 are each independently hydrogen; halogen; alkyl having 1 to 20 carbon atoms; alkenyl having 2 to 20 carbon atoms; aryl having 6 to 20 carbon atoms; alkylaryl having 6 to 20 carbon atoms; arylalkyl having 7 to 20 carbon atoms; alkyl amido having 1 to 20 carbon atoms; aryl amido having 6 to 20 carbon atoms; or alkylidene having 1 to 20 carbon atoms, R1 is hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms;

R2 and R3 are each independently hydrogen; silyl; alkyl having 1 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; or a metalloid radical of a metal in group 14, substituted with hydrocarbyl having 1 to 20 carbon atoms;

R2 and R3 may be connected to each other to form an aliphatic ring having 5 to 20 carbon atoms or an aromatic ring having 6 to 20 carbon atoms;

the aliphatic ring or the aromatic ring is halogen, alkyl having 1 to 20 carbon atoms, alkenyl having 2 to 20 carbon atoms, or aryl having 6 to 20 carbon atoms, and R4 to R16 are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms According to another aspect of the present invention, there is provided a catalyst composition including the transition metal compound represented by the above Formula 1.

According to further another aspect of the present invention, there is provided a preparation method of a polymer using the catalyst composition.

Advantageous Effects

The transition metal compound according to the present invention may be used as a catalyst having good copolymerization properties due to the formation of a condensed ring by an amido ligand and ortho-phenylene and an amine heteroatom introduced in a five-membered ring pi-ligand combined with the ortho-phenylene, and a polymer having a discriminating molecular weight may be prepared by using thereof.

BEST MODE FOR CARRYING OUT THE INVENTION

Figure 1:
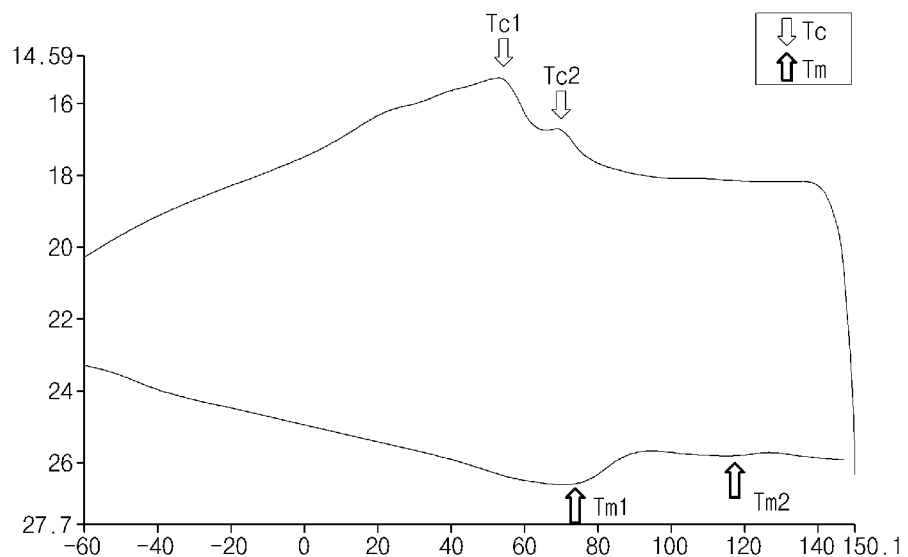
FIG. 1 is a differential scanning calorimeter (DSC) graph of a polymer prepared in Example 1 of the present invention.

According to an aspect of the present invention, a transition metal compound represented by the following Formula 1 is provided.

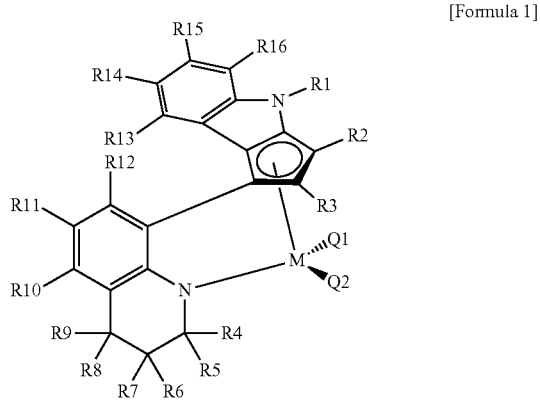

[Formula 1]

in the above Formula 1,

M is a transition metal in group 4,

Q1 and Q2 are each independently hydrogen; halogen; alkyl having 1 to 20 carbon atoms; alkenyl having 2 to 20 carbon atoms; aryl having 6 to 20 carbon atoms; alkylaryl having 6 to 20 carbon atoms; arylalkyl having 7 to 20 carbon atoms; alkyl amido having 1 to 20 carbon atoms; aryl amido having 6 to 20 carbon atoms; or alkylidene having 1 to 20 carbon atoms, R1 is hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms;

R2 and R3 are each independently hydrogen; silyl; alkyl having 1 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; or a metalloid radical of a metal in group 14, substituted with hydrocarbyl having 1 to 20 carbon atoms;

R2 and R3 may be connected to each other to form an aliphatic ring having 5 to 20 carbon atoms or an aromatic ring having 6 to 20 carbon atoms;

the aliphatic ring or the aromatic ring is halogen, alkyl having 1 to 20 carbon atoms, alkenyl having 2 to 20 carbon atoms, or aryl having 6 to 20 carbon atoms, and R4 to R16 are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms.

In the transition metal compound represented by Formula 1 described in the present disclosure, a metal site is connected to a cyclopentadienyl (Cp) ligand introducing an amido group connected to a phenylene bridge as a ring shape, and the structure thereof has a narrow Cp-M-N angle and a wide Q1-M-Q2 angle to which a monomer may approach. Thus, cyclopentadiene, a phenylene bridge, nitrogen and the metal site are connected in order, and more stable and rigid pentagonal ring structure may be formed. In addition, in the structure of the compound represented by the above Formula 1, nitrogen (N) atom of a heterocycle is combined at position 3 of the cyclopentadiene, thereby increasing activity and controlling the molecular weight of a polymer prepared when used as a catalyst. Accordingly, the transition metal compound of represented by above Formula 1 may produce a polymer having good copolymerization properties and discriminating molecular weight. In an embodiment, when applying the compounds for the polymerization of olefin after reacting with a co-catalyst such as methyl aluminoxane or B(C6F5)3 and activating, polyolefin having high activity, high molecular weight and high copolymerization degree may be produced at a high polymerization temperature. Particularly, since a large amount of alpha-olefin may be introduced as well as a linear polyethylene having a low density of 0.875-0.91 g/cc due to the structural characteristics of the catalyst, a polyolefin copolymer having an extremely low density of less than 0.91 g/cc may be produced. In particular, a polymer having narrow molecular weight distribution (MWD, hereinafter abbreviated as 'MWD') with respect to a constrained-geometry catalyst (CGC, hereinafter abbreviated as 'CGC'), good copolymerization properties and high molecular weight in a low density region may be prepared by using a catalyst composition including the transition metal compound. Particularly, the compound represented by Formula 1 may control the structure and physical properties of the polyolefin thus produced by easily controlling electronic and steric environment around a metal. The compound represented by the above Formula 1 may preferably be used for preparing a catalyst for polymerizing an olefin monomer, however the present invention is not limited thereto. The transition metal compound may be used in any other applicable fields.

In the present disclosure, alkyl and alkenyl may be a linear or branched chain alkyl or alkenyl.

In the present disclosure, aryl includes a monocyclic aryl or a polycyclic aryl, for example, phenyl, naphthyl, anthryl, phenanthryl, crysenyl, pyrenyl, etc.

According to an embodiment of the present disclosure, Q1 and Q2 are each independently hydrogen, halogen or alkyl having 1 to 20 carbon atoms, and R1 to R16 are each independently hydrogen or alkyl having 1 to 20 carbon atoms.

According to an embodiment of the present disclosure, Q1 and Q2 are each independently alkyl having 1 to 6 carbon atoms, R1, R4 and R5 are each independently hydrogen or alkyl having 1 to 6 carbon atoms, and R2, R3 and R6 to R16 are hydrogen.

According to an embodiment of the present disclosure, Q1, Q2 and R1 are alkyl having 1 to 6 carbon atoms, and R2 to R16 are hydrogen.

According to an embodiment of the present disclosure, Q1, Q2 and R1 are alkyl having 1 to 6 carbon atoms, R4 and R5 are each independently hydrogen or alkyl having 1 to 6 carbon atoms, both R4 and R5 are not hydrogen at the same time, and R2, R3, and R6 to R16 are hydrogen.

According to an embodiment of the present disclosure, R1, R4 and R5 are hydrogen or methyl, and R2, R3, and R6 to R16 are hydrogen.

According to an embodiment of the present disclosure, at least one of R1, R4 and R5 are alkyl having 1 to 20 carbon atoms, and R2, R3 and R6 to R16 are hydrogen.

According to an embodiment of the present disclosure, R1 is alkyl having 1 to 20 carbon atoms, and R2 to R16 are hydrogen.

According to an embodiment of the present disclosure, R1 is alkyl having 1 to 6 carbon atoms, and R2 to R16 are hydrogen.

According to an embodiment of the present disclosure, R1 is methyl, at least one of R4 and R5 is methyl and the remainder is hydrogen, and R2, R3, R6 to R16 are hydrogen.

R1 is methyl, at least one of R4 or R5 is methyl and the remainder is hydrogen, and in case of R2, R3 and R6 to R16 are hydrogen, the transition metal compound represented by Formula 1 may be a racemic body of (R) and (S).

In the disclosure, the racemic body (or racemic mixture) is a mixture of an enantiomer having right-handed rotation and an enantiomer having left-handed rotation, where (R) means right-handed rotation and (S) means left-handed rotation.

According to an embodiment of the present disclosure, M is Ti, Hf or Zr.

According to an embodiment of the present disclosure, M is Ti.

According to an embodiment of the present disclosure, Q1 and Q2 are methyl.

According to an embodiment of the present disclosure, the transition metal compound represented by Formula 1 may be a compound represented by the following Formula 2 or Formula 3, or a mixture thereof.

[Formula 2]

[Formula 3]

Here, the compound represented by Formula 3 may be a racemic body, and the ratio (R):(S) of the racemic body of the compound represented by Formula 3 may be 1:99 to 99:1.

The transition metal compound according to an embodiment of the present invention may be prepared by the following Reaction 1. The following Reaction 1 illustrates the synthetic process of the transition metal compound, and for example a synthetic process of the transition metal compound represented by Formula 3.

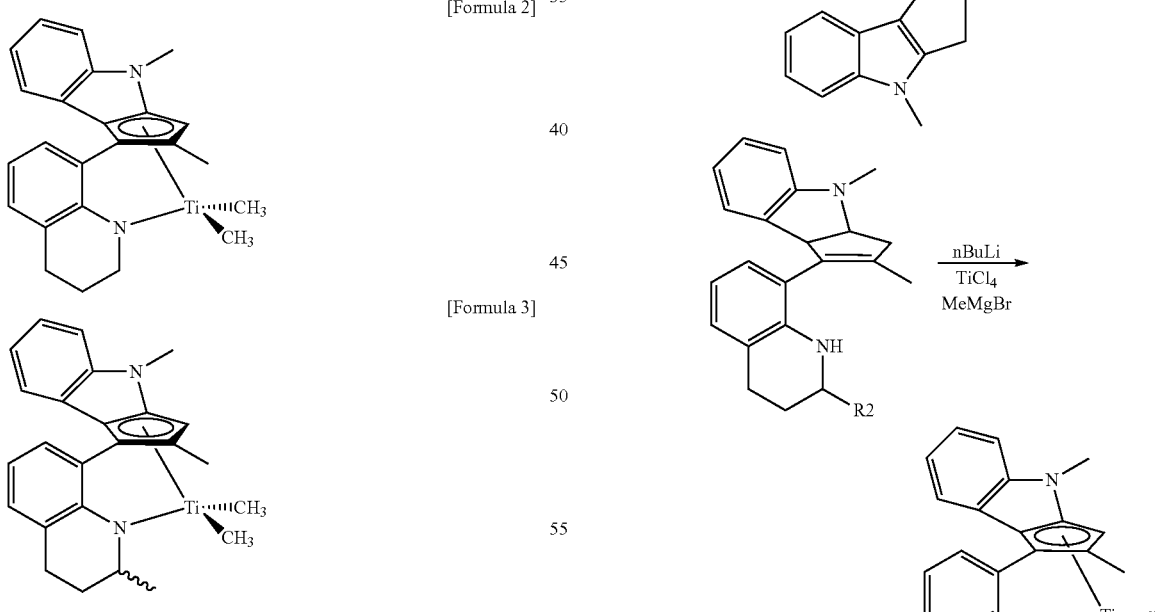

[Reaction 1]

In the above Reaction 1, the substituents are the same as defined in Formula 1.

The present disclosure also provides a catalyst composition including the transition metal compound represented by Formula 1.

The catalyst composition may further include a co-catalyst. The co-catalyst may be any material known in this art.

For example, the catalyst composition may further include at least one of the following Formulae 4 to 6.

—[Al(R3)-O]a-           [Formula 4]

In the above formula, R3 is independently a halogen radical; a hydrocarbyl radical having 1 to 20 carbon atoms; or a halogen substituted hydrocarbyl radical having 1 to 20 carbon atoms; and a is an integer of at least 2.

D(R4)3           [Formula 5]

In the above formula, D is aluminum or boron; R4 is independently a halogen radical; a hydrocarbyl radical having 1 to 20 carbon atoms; or a halogen substituted hydrocarbyl radical having 1 to 20 carbon atoms.

[L-H]+[Z(A)4]- or [L]+[Z(A)4]-           [Formula 6]

In the above formula, L is a neutral or a cationic Lewis acid; H is a hydrogen atom; Z is an element in group 13; each A is independently aryl having 6 to 20 carbon atoms or alkyl having 1 to 20 carbon atoms, where at least one hydrogen atom may be substituted with a substituent; and the substituent is halogen, hydrocarbyl having 1 to 20 carbon atoms, alkoxy having 1 to 20 carbon atoms or aryloxy having 6 to 20 carbon atoms.

As a preparation method of the catalyst composition, a first preparation method including a step of obtaining a mixture by contacting the transition metal compound represented by the above Formula 1 with the compound represented by the above Formula 4 or 5; and a step of adding a compound represented by the above Formula 6 in the mixture is provided.

A second preparation method of the catalyst composition by contacting the transition metal compound represented by the above Formula 1 and the compound represented by the above Formula 6, is provided.

In the first method of the preparation methods of the catalyst composition, the molar ratio of the compound represented by the above Formula 4 or 5 with respect to the transition metal compound represented by the above Formula 1 is preferably from 1:2 to 1:5,000, more preferably, from 1:10 to 1:1,000, and most preferably, from 1:20 to 1:500.

Meanwhile, the molar ratio of the compound represented by Formula 7 with respect to the transition metal compound represented by Formula 1 is preferably from 1:1 to 1:25, more preferably, from 1:1 to 1:10, and most preferably, from 1:1 to 1:5.

In the case that the molar ratio of the compound represented by the above Formula 4 or 5 with respect to the transition metal compound represented by Formula 1 is less than 1:2, the amount of an alkylating agent is very small, and the alkylation of the metal compound may be incompletely performed, and in the case that the molar ratio exceeds 1:5,000, the alkylation of the metal compound may be performed, however a side reaction between the remaining alkylating agent and the activating agent of the above Formula 6 may be performed, and the activation of the alkylated metal compound may be incompletely performed. In addition, in the case that the molar ratio of the compound represented by Formula 6 with respect to the transition metal compound represented by Formula 1 is less than 1:1, the amount of the activating agent is relatively small, the activation of the metal compound may be incompletely performed, and the activity of the catalyst composition may be deteriorated, and in the case that the molar ratio exceeds 1:25, the activation of the metal compound may be completely performed, however the excessive activating agent remained may increase the production cost of the catalyst composition, or the purity of the polymer thus prepared may be deteriorated.

In the second method of the preparation methods of the catalyst composition, the molar ratio of the compound represented by the above Formula 6 with respect to the transition metal compound represented by the above Formula 1 is preferably from 1:1 to 1:500, more preferably, from 1:1 to 1:50, and most preferably, from 1:2 to 1:25. In the case that the molar ratio is less than 1:1, the amount of the activating agent is relatively small, the activation of the catalyst composition may be incompletely performed, and the activity of the catalyst composition thus prepared may be deteriorated, and in the case that the molar ratio exceeds 1:500, the activation of the metal compound may be completely performed, however the excessive activating agent remained may increase the unit cost of the catalyst composition, or the purity of the polymer thus prepared may be deteriorated.

As a reaction solvent used during the preparation of the composition, a hydrocarbon solvent such as pentane, hexane, heptane, etc, or an aromatic solvent such as benzene, toluene, etc. may be used, however the present invention is not limited thereto, and all solvents used in this field may be used.

In addition, the transition metal compound represented by Formula 1 and the co-catalyst may be used as a supported type by a support. Silica or alumina may be used as the support.

The compound represented by the above Formula 4 is not specifically limited only if alkylaluminoxane is used. Preferably, the compound includes methylaluminoxane, ethylaluminoxane, isobutylaluminoxane, butylaluminoxane, etc., and the methylaluminoxane is a particularly preferable compound.

The compound represented by the above Formula 5 is not specifically limited and includes trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, etc., and particularly preferable compound is selected from the trimethylaluminum, the triethylaluminum, and the triisobutylaluminum.

Examples of the compound represented by the above Formula 6 includes triethylammoniumtetraphenylboron, tributylammoniumtetraphenylboron, trimethylammoniumtetraphenylboron, tripropylammoniumtetraphenylboron, trimethylammoniumtetra(p-tolyl)boron, trimethylammoniumtetra(o,p-dimethylphenyl)boron, tributylammoniumtetra (p-trifluoromethylphenyl)boron, trimethylammoniumtetra (p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra(p-trifluoromethylphenyl)aluminum, tributylammoniumtetrapentafluorophenylaluminum, N,N-diethylaniliniumtetraphenylaluminum, N,N-diethylaniliniumtetraphenylaluminum, N,N-diethylaniliniumtetrapentafluorophenylaluminum, diethylammoniumtetrapentatetraphenylaluminum, triphenylphosphoniumtetraphenylaluminum, trimethylphosphoniumtetraphenylaluminum, triethylammoniumtetraphenylaluminum, tributylammoniumtetraphenylaluminum, trimethylammoniumtetraphenylboron, tripropylammoniumtetraphenylboron, trimethylammoniumtetra(p-tolyl)boron, tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, triphenylcarboniumtetra(p-trifluoromethylphenyl)boron, triphenylcarboniumtetrapentafluorophenylboron, etc.

A polyolefin homopolymer or copolymer may be prepared by contacting the catalyst composition including the transition metal compound represented by Formula 1; and at least one compound selected from the compounds represented by Formulae 4 to 6, with at least one olefin monomer.

The most preferable preparation process using the catalyst composition is a solution process. In the case that the composition is used together with an inorganic support such as silica, a slurry process or a gas phase process may be also applied.

In the preparation process, the activating catalyst composition may be injected after being dissolved or diluted in an aliphatic hydrocarbon solvent having 5 to 12 carbon atoms such as pentane, hexane, heptane, nonane, decane and an isomer thereof, an aromatic hydrocarbon solvent such as toluene and benzene, or a hydrocarbon solvent substituted with a chlorine atom such as dichloromethane and chlorobenzene. The solvent may preferably be used after removing a small amount of water or air, which functions as a catalyst poison, by treating with a small amount of alkylaluminum, and may be used by further using a co-catalyst.

The olefin monomer polymerizable using the metal compound and the co-catalyst may include ethylene, an alpha-olefin, a cyclic olefin, etc., and a diene olefin monomer, a triene olefin monomer, etc. having at least two double bonds may also be polymerized. Particular examples of the monomer may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-icosene, norbornene, norbornadiene, ethylidenenorbornene, phenylnorbornene, vinylnorbornene, dicyclopentadiene, 1,4-butadiene, 1,5-pentadiene, 1,6-hexadiene, styrene, alpha-methylstyrene, divinylbenzene, 3-chloromethylstyrene, etc. A mixture of at least two of these monomers may be copolymerized.

Particularly, in the preparation method of the present invention using the catalyst composition, a copolymer having high molecular weight and a polymer density of less than or equal to 0.91 g/cc may be prepared in a copolymerization reaction of monomers such as ethylene and 1-octene having large steric hindrance at high reaction temperature greater than or equal to 90° C.

According to an aspect, the polymer prepared by the preparation method of the present invention has a density of 0.875 to 0.91 g/cc.

In addition, the polymer prepared by the preparation method of the present invention includes Tm1 and Tm2, which are melting temperatures (TM) obtained from a DSC curve. In a density region of 0.875 to 0.91 g/cc of the olefin polymer, Tm1 may be in a range of 60 to 80° C., and Tm2 may be in a range of 100 to 120° C.

Further, the olefin polymer includes Tc1 and Tc2, which are crystallization temperatures (Tc) obtained from a DSC curve obtained by measuring using a DSC. In a density region of 0.875 to 0.91 g/cc of the olefin polymer, Tc1 may be in a range of 50 to 70° C., and Tc2 may be in a range of 60 to 80° C.

In the case where a polymer is prepared using a common metallocene catalyst, one Tm or one Tc is present. However, in the case where two Tms are present, a crystal may be molten and crystallized at different temperatures, and thermal stability and mechanical strength may be increased.

In addition, in case of using at least two kinds of hybrid catalysts, two Tms may be present. However, in this case, the anticipation and control of the activity and copolymerization properties of each of the hybrid catalysts may be difficult, and the preparation of an olefin-based polymer having appropriate properties according to use may be difficult. In addition, at least two kinds of catalyst components may not be blended homogeneously, and the control of quality may become difficult.

Tm and Tc used in the present disclosure mean values shown in a graph of temperature-heat flux of DSC.

Hereinafter, the present invention will be explained more particularly referring to the following embodiments. The embodiments are for assisting the understanding of the present invention, and the scope of the present invention is not limited thereto.

Organic reagents and solvents were purchased from Aldrich Co. and used after purifying by a standard method unless otherwise mentioned. In all steps of syntheses, air and humidity were blocked to increase the reproducibility of experiments.

Synthesis of Transition Metal Compound
Synthesis of Ketone Compound

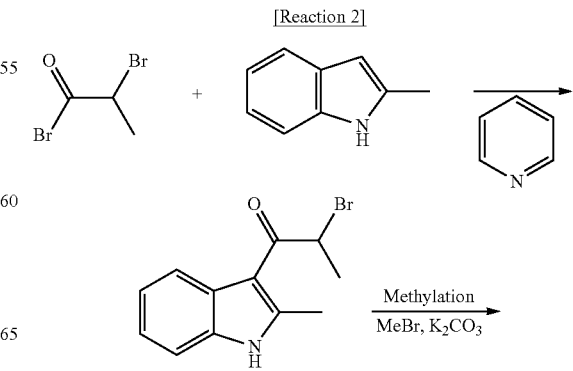

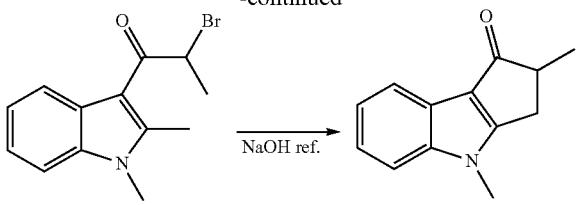

The synthesis was performed according to the steps in Reaction 2 referring to a document [1973 Tegrahedron 29, 971-979].

$^1$H NMR (CDCl$_3$): δ 1.41 (s, 3H, Cp-CH$_3$), 2.67-2.618 (dd, 1H, CH), 3.095-3.016 (dt, 1H, CH), 3.320-3.272 (dd, 1H, CH), 3.739 (s, 3H, N—CH$_3$), 7.952-7.277 (m, 4H, aromatic), ppm Synthesis of Ligand Synthetic Example 1

To 1,2,3,4-tetrahydroquinoline (1 g, 6.8 mmol) dissolved in 10 mL of ether, n-butyllithium (1.1 eq.) was slowly added drop by drop at −40° C. The temperature was slowly elevated to room temperature, followed by stirring at room temperature for 4 hours. The temperature was decreased to −40° C. again, and CO2 (g) was injected thereto, followed by maintaining the reaction at a low temperature for 0.5 hours. The temperature was slowly elevated, and remaining CO2 (g) was removed using a bubbler. tBuLi (1.3 eq) was inserted at −20° C., followed by aging at a low temperature of −20° C. for 2 hours. The above ketone compound (3 mmol) was dissolved in a diethyl ether solution and slowly added drop by drop. After stirring for 12 hours at room temperature, 10 mL of water was injected and hydrochloric acid (2N, 20 mL) was added, followed by stirring for 2 minutes. Organic solvents were extracted and neutralized with a NaHCO3 aqueous solution. Organic solvents were extracted, and water was removed with MgSO4. Through recrystallization, a ligand compound represented by the following Formula 8 was obtained as a yellow solid (30% yield).

[Formula 8]

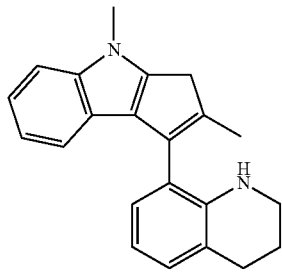

$^1$H NMR (CDCl$_3$): δ 1.244-1.229 (s, 3H, Cp-CH$_3$), 1.719-1.679 (m, 1H, quinolineN-CH$_2$), 2.495-2.468 (t, 2H, quinolineN-CH$_2$), 2.599 (s, 3H, N—CH$_3$), 2.680-2.639 (m, 1H, quinolineN—CH$_2$), 2.780-4.430 (m, 1H, quinolineN—CH$_2$), 6.985-6.282 (m, 4H, aromatic), 7.112-7.096 (m, 2H, aromatic), 8.18-8.16 (t, 1H, aromatic) ppm.

Synthetic Example 2

To 2-methyl-1,2,3,4-tetrahydroquinoline (1 g, 6.8 mmol) dissolved in 10 mL of ether, n-butyllithium (7.48 mmol, 1.1 eq.) was slowly added drop by drop at −40° C. The temperature was slowly elevated to room temperature, followed by stirring at room temperature for 4 hours. The temperature was decreased to −40° C. again, and 002(g) was injected thereto, followed by maintaining the reaction at a low temperature for 0.5 hours. The temperature was slowly elevated, and remaining 002(g) was removed using a bubbler. tBuLi (8.84 mmol, 1.3 eq) was injected at −20° C., followed by aging at a low temperature of −20° C. for 2 hours. The above ketone compound (3 mmol) was dissolved in a diethyl ether solution and slowly added drop by drop. After stirring for 12 hours at room temperature, 10 mL of water was added and hydrochloric acid (2N, 20 mL) was added, followed by stirring for 2 minutes. Organic solvents were extracted and neutralized with a NaHCO3 aqueous solution. Organic solvents were extracted, and water was removed with MgSO4. Through recrystallization, a ligand compound represented by the following Formula 9 was obtained as a yellow solid (30% yield).

[Formula 9]

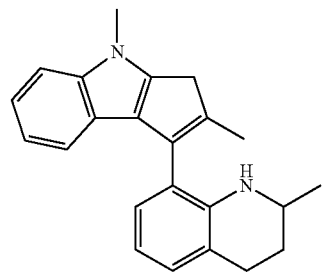

$^1$H NMR (CDCl$_3$): δ 0.731-0.718 (s, 1H, N—C—CH$_3$), 0.793-0.781 (s, 3H, Cp-CH$_3$), 2.932-1.491 (m, 7H, quinolineN—CH$_2$, Cp-CH$_2$), 2.969 (s, 3H, N—CH$_3$), 7.383-6.279 (m, 6H, aromatic), 7.756-7.726 (t, 1H, aromatic) ppm.

Synthesis of Transition Metal Compound

Preparation Example 1

N-butyllithium (0.255 mmol, 2.1 eq.) was slowly added drop by drop to the ligand compound prepared in Synthetic Example 1 (100 mg, 0.304 mmol) at 20° C. The formation of a yellow slurry was observed, and the temperature was slowly elevated to room temperature, followed by stirring at room temperature for 12 hours. An additive for increasing solubility was added and TiCl4 (1.0 eq.) was added drop by drop, followed by stirring at room temperature for 12 hours. After that, NeMgBr (2.1 eq.) was added, solvents were removed, and the remaining product was extracted with toluene to produce a transition metal compound represented by the following Formula 2 as an orange solid (50% yield).

[Formula 2]

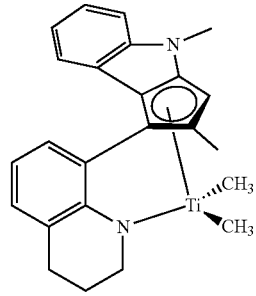

¹H NMR (CDCl₃): δ-0.667 (s, 3H, Ti—CH₃), 0.441 (s, 3H, Ti—CH₃), 1.945 (s, 3H, Cp-CH₃), 1.932 (m, 2H, quinoline-NCH₂), 2.746-2.721 (t, 2H, quinolineN—CH₂), 3.789 (s, 3H, N—CH₂), 4.657-4.610 (m, 1H, quinolineN—CH₂), 4.666-4.430 (m, 1H, quinolineN—CH₂), 7.271-6.814 (d, 7H, aromatic) ppm.

Preparation Example 2

N-butyllithium (0.255 mmol, 2.1 eq.) was slowly added drop by drop to the ligand compound (100 mg, 0.304 mmol) prepared in Synthetic Example 2 at 20° C. The formation of a yellow slurry was observed, and the temperature was slowly elevated to room temperature, followed by stirring at room temperature for 12 hours. An additive for increasing solubility was added and TiCl4 (1.0 eq.) was added drop by drop, followed by stirring at room temperature for 12 hours. After that, MeMgBr (2.1 eq.) was added, solvents were removed, and the remaining product was extracted with toluene to produce a transition metal compound represented by the following Formula 3 as an orange solid (50% yield).

[Formula 3]

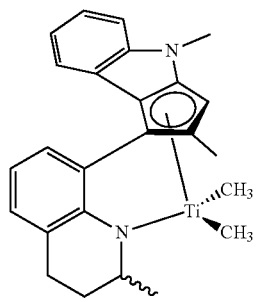

¹H NMR (CDCl₃) mixture of stereoisomer: δ 1.46-1.467 (t, 2H, quinoline-NCH₂), 1.81 (s, 3H, Cp-CH₃), 2.10-2.07 (t, 2H, quinoline-NCH₂), 4.45-4.41 (m, 2H, N—CH₂), 4.53-4.50 (m, 2H, N—CH₂), 6.00 (Cp, 1H), 6.38-6.37 (d, 1H, aromatic) 6.70-6.69 (d, 1H, aromatic) 6.85-6.83 (m, 2H, aromatic) 6.98-6.96 (d, 1H, aromatic) ppm.

Comparative Preparation Example 1

A transition metal compound represented by the following Formula 10 was prepared referring to the contents described in European Patent Nos. 416,815 and 414,848.

[Formula 10]

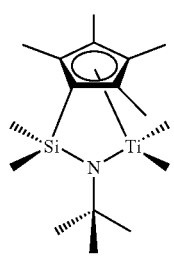

¹H NMR (C₆D₆): δ 2.00 (s, 6H), 1.99 (s, 6H), 1.42 (s, 9H), 0.43 (s, 6H) ppm.

Comparative Preparation Example 2

A transition metal compound represented by the following Formula 11 was prepared referring to the contents described in U.S. Pat. No. 7,928,256.

[Formula 11]

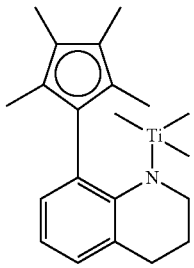

¹H NMR (C₆D₆): δ 7.00 (d, J=7.6 Hz, 1H), 9.92 (d, J=7.6 Hz, 1H), 6.83 (t, J=7.6 Hz, 1H), 4.53 (m, 2H), 2.47 (t, J=6.4 Hz, 2H), 2.05 (s, 6H), 1.66 (s, 6H), 1.76-1.65 (m, 2H), 0.58 (s, 6H) ppm.

Comparative Preparation Example 3

A transition metal compound represented by the following Formula 12 was prepared referring to the contents described in Korean Patent Publication No. 986,301.

[Formula 12]

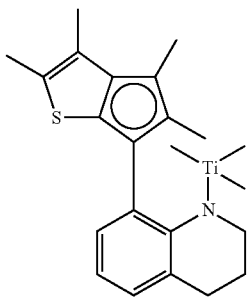

¹H NMR (C₆D₆): δ 7.10 (d, J=7.2 Hz, 1H), 6.91 (d, J=7.2 Hz, 1H), 6.81 (t, J=7.2 Hz, 1H), 4.58 (dt, J=14, 5.2 Hz, 1H, NCH₂), 4.42 (dt, J=14, 5 Hz, 1H, NCH₂), 2.50-2.38 (m, 2H, CH₂), 2.32 (s, 3H), 2.11 (s, 3H), 2.00 (s, 3H), 1.71 (s, 3H), 1.67 (quintet, J=5.2 Hz, CH₂), 0.72 (s, 3H, TiMe), 0.38 (s, 3H, TiMe) ppm.

Preparation Example of Polymer

Polymers were prepared using each transition metal compound prepared in Examples 1 and 2 and Comparative Examples 1 to 3.

Example 1

A hexane solvent (1.0 L) and 1-octene (0.84 M) were inserted in a 2 L autoclave reactor, followed by pre-heating the reactor to 150° C. At the same time, the pressure of the reactor was filled up with ethylene (35 bar) in advance. A transition metal compound (2.0 μmol) of Preparation Example 1 treated with a triisobutyl aluminum compound and a dimethylanilinium tetrakis(pentafluorophenyl)borate co-catalyst (20 μmol) were injected to the reactor one by one while pressurizing using argon with high pressure (molar ratio of Al:Ti=10:1). Then, a copolymerization reaction was performed for 8 minutes. After that, the remaining ethylene gas was exhausted, and a polymer solution was added to an excessive amount of ethanol to induce precipitation. The precipitated polymer was washed with ethanol and acetone twice or three times, respectively, and dried in a vacuum oven at 80° C. for more than 12 hours to prepare a polymer.

Example 2

A polymer was prepared through the same method described in Example 1 except for using the transition metal compound of Preparation Example 2 instead of the transition metal compound of Preparation Example 1.

Comparative Example 1

A polymer was prepared through the same method described in Example 1 except for using the transition metal compound of Comparative Preparation Example 1 instead of the transition metal compound of Preparation Example 1.

Comparative Example 2

A polymer was prepared through the same method described in Example 1 except for using the transition metal compound of Comparative Preparation Example 2 instead of the transition metal compound of Preparation Example 1.

Comparative Example 3

A polymer was prepared through the same method described in Example 1 except for using the transition metal compound of Comparative Preparation Example 3 instead of the transition metal compound of Preparation Example 1 and decreasing the inner temperature of the reactor to 120° C.

EXPERIMENTAL EXAMPLE

Figure 2:
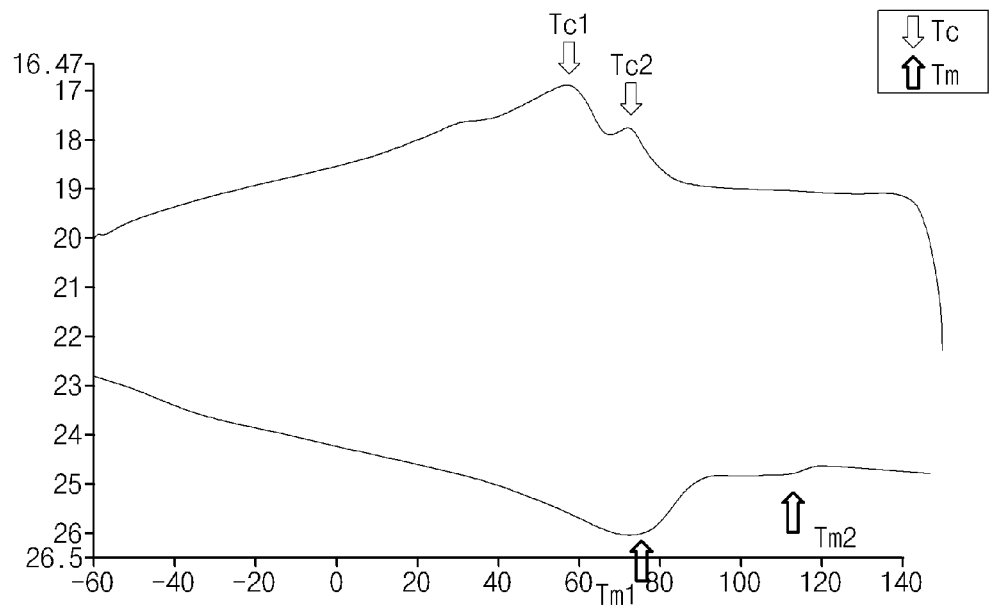
FIG. 2 is a differential scanning calorimeter (DSC) graph of a polymer prepared in Example 2 of the present invention.
Figure 3:
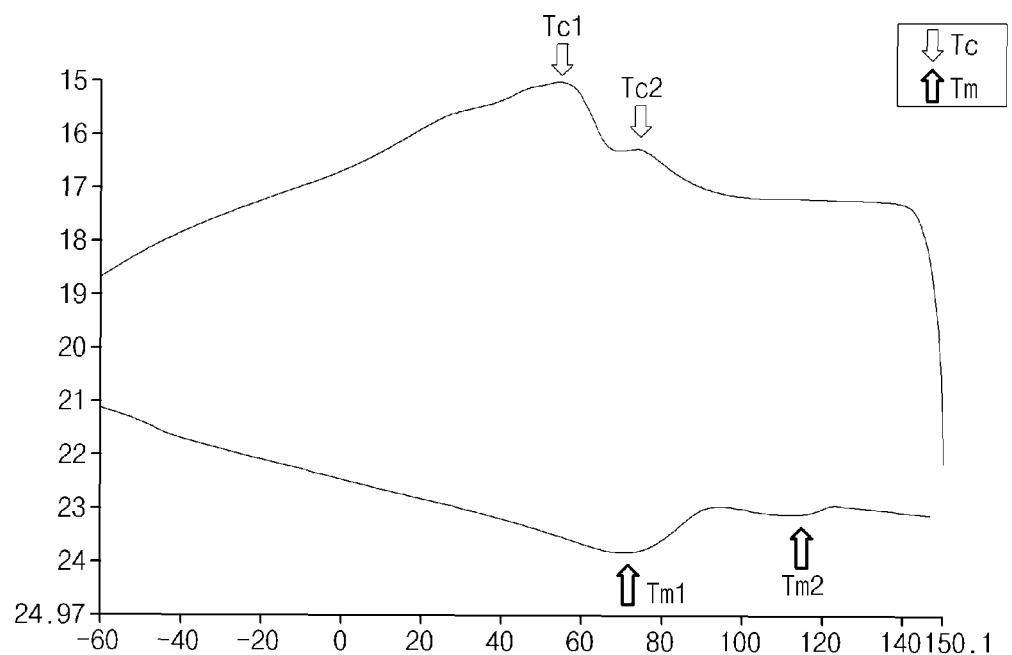
FIG. 3 is a differential scanning calorimeter (DSC) graph of a polymer prepared in Example 3 of the present invention.

The physical properties of each polymer prepared in Example 1, Example 2, and Comparative Examples 1 to 3 were compared and analyzed. Evaluation results are shown in the following Table 1, Table 2 and FIGS. 1 to 3.

1) Melt Index (MI)

Melt index (MI) of each polymer was measured according to ASTM D-1238 (condition E, 190° C., 2.16 kg load).

2) Melting Temperature (Tm) and Crystallization Temperature (Tc)

The melting temperature and the crystallization temperature of each polymer were obtained using a differential scanning calorimeter 2920 (DSC) manufactured by TA Co. Particularly, 1 mg of each polymer was filled, and a nitrogen gas flow rate was controlled to 20 ml/min. In order to synchronize the thermal hysteresis of each polymer, the temperature of each polymer was increased from 0° C. to 150° C. with a rate of 20° C./min. Then, measurement was conducted while increasing the temperature from 150° C. to −100° C. with a rate of 10° C./min and then, elevating from −100° C. to 150° C. with a rate of 10° C./min.

3) Density (g/cc)

The density of each polymer was obtained after manufacturing a sheet having a thickness of 3 mm and a radius of 2 cm using a press mold at 190° C., and annealing at room temperature for 24 hours, and measuring using a Mettler balance.

TABLE 1

| Division | MI (g/10 min) | D (g/cc) | Tc (° C.) Tc1 | Tc (° C.) Tc2 | Tm (° C.) Tm1 | Tm (° C.) Tm2 |
|---|---|---|---|---|---|---|
| Example 1 | 9.43 | 0.881 | 53.40 | 69.88 | 73.91 | 117.48 |
| Example 2 | 0.24 | 0.885 | 58.71 | 73.02 | 73.92 | 111.11 |
| Comparative Example 1 | 25.25 | 0.904 | 64.34 | | 102.34 | |
| Comparative Example 2 | 7.59 | 0.871 | 40.08 | | 58.06 | |

TABLE 2

| Division | Yield (g) | D (g/cc) | Tc (° C.) Tc1 | Tc (° C.) Tc2 | Tm (° C.) Tm1 | Tm (° C.) Tm2 |
|---|---|---|---|---|---|---|
| Example 2 | 42.9 | 0.885 | 58.71 | 73.02 | 73.92 | 111.11 |
| Comparative Example 3 | 42.0 | 0.890 | (39.1) | 69.4 | 87 | |

As shown in Table 1, the polymers of Examples 1 and 2 prepared using the catalyst composition including the transition metal compound according to an embodiment of the inventive concept generally have low density region and high molecular weight when compared to the polymers of Comparative Examples 1 and 3 prepared using a catalyst composition including a common transition metal compound.

In addition, for the polymers of Examples 1 and 2, two values for each of Tc and Tm were measured, however for the polymers of Comparative Examples 1 and 3, one value for each of Tc and Tm was measured.

Also, as shown in Table 2, the polymer of Example 2 prepared using the catalyst composition including the transition metal compound according to an embodiment of the inventive concept was prepared with higher yield and had two values for each of Tc and Tm when compared to the polymer of Comparative Example 3 prepared using a catalyst composition including the transition metal compound of Comparative Preparation Example 3.

Particularly, it is known that catalyst activity is deteriorated and yield is not good when preparing a polymer via polymerization at a high polymerization temperature. However, the polymer of Example 2 according to an embodiment of the present invention was prepared with high yield even though prepared at a high polymerization temperature of 150° C. when compared to the polymer of Comparative Example 3 prepared via polymerization at a low polymerization temperature of 120° C. From the result, high activity may be obtained even though the catalyst composition including the transition metal compound according to an embodiment of the inventive concept is used in polymerization at a high temperature. As shown in the above results, the catalyst composition including the transition metal compound according to an embodiment of the present invention has good activity during polymerization at a high temperature, and a polymer having a high molecular weight may be prepared in a low density region. In addition, a polymer having two values of each of Tc and Tm may be prepared when preparing a polymer using the catalyst composition. Accordingly, the polymer may be molten and crystallized at different temperatures, thereby improving thermal stability and mechanical strength.

The invention claimed is:

1. A transition metal compound represented by the following Formula 1:

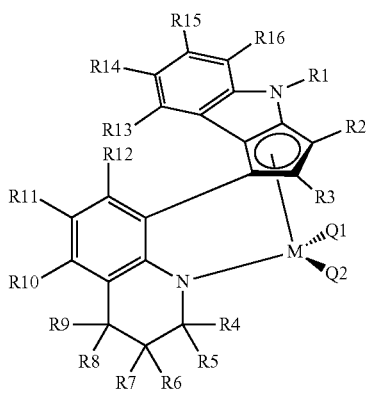

[Formula 1]

in the above Formula 1,

M is a transition metal in group 4, $Q_1$ and $Q_2$ are each independently hydrogen; halogen; alkyl having 1 to 20 carbon atoms; alkenyl having 2 to 20 carbon atoms; aryl having 7 to 20 carbon atoms; alkylaryl having 6 to 20 carbon atoms; arylalkyl having 7 to 20 carbon atoms; alkyl amido having 1 to 20 carbon atoms; or aryl amido having 6 to 20 carbon atoms;

$R_1$ is hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms;

$R_2$ and $R_3$ are each independently hydrogen; silyl; alkyl having 1 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; or a metalloid radical of a metal in group 14, substituted with hydrocarbyl having 1 to 20 carbon atoms;

$R_2$ and $R_3$ are optionally connected to each other to form an aliphatic ring having 5 to 20 carbon atoms or an aromatic ring having 6 to 20 carbon atoms, wherein the aliphatic ring or the aromatic ring is optionally substituted with halogen, alkyl having 1 to 20 carbon atoms, alkenyl having 2 to 20 carbon atoms, or aryl having 6 to 20 carbon atoms, and $R_4$ to $R_{16}$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms.

2. The transition metal compound of claim 1, wherein $Q_1$ and $Q_2$ are each independently hydrogen, halogen or alkyl having 1 to 20 carbon atoms, and $R_1$ to $R_{16}$ are each independently hydrogen or alkyl having 1 to 20 carbon atoms.

3. The transition metal compound of claim 1, wherein $Q_1$ and $Q_2$ are each independently alkyl having 1 to 6 carbon atoms, $R_1$, $R_4$ and $R_5$ are each independently hydrogen or alkyl having 1 to 6 carbon atoms, and $R_2$, $R_3$ and $R_6$ to $R_{16}$ are hydrogen.

4. The transition metal compound of claim 1, wherein $Q_1$, $Q_2$ and $R_1$ are alkyl having 1 to 6 carbon atoms, and $R_2$ to $R_{16}$ are hydrogen.

5. The transition metal compound of claim 1, wherein $Q_1$, $Q_2$ and $R_1$ are alkyl having 1 to 6 carbon atoms, $R_4$ and $R_5$ are each independently hydrogen or alkyl having 1 to 6 carbon atoms, both $R_4$ and $R_5$ are not hydrogen at the same time, and $R_2$, $R_3$ and $R_6$ to $R_{16}$ are hydrogen.

6. The transition metal compound of claim 1, wherein M is Ti, Hf or Zr.

7. The transition metal compound of claim 1, wherein the transition metal compound represented by Formula 1 is a compound represented by the following Formula 2 or Formula 3:

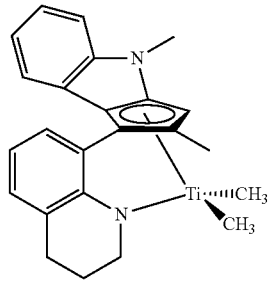

[Formula 2]

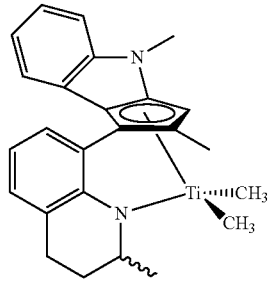

[Formula 3]

where the compound of Formula 3 is a racemic body of (R) and (S).

8. A catalyst composition comprising the transition metal compound according to claim 1.

9. The catalyst composition of claim 8, further comprising at least one kind of a co-catalyst.

10. The catalyst composition of claim 9, wherein the co-catalyst comprises at least one selected from the following Formulae 4 to 6:

—[Al(R$_{22}$)—O]$_a$—      [Formula 4]

in the above formula, each $R_{22}$ is independently a halogen radical; a hydrocarbyl radical having 1 to 20 carbon atoms; or a halogen substituted hydrocarbyl radical having 1 to 20 carbon atoms; and a is an integer of at least 2;

D(R$_{22}$)$_3$      [Formula 5]

in the above formula, D is aluminum or boron; and each $R_{22}$ is the same as described above;

[L-H]$^+$[Z(A)$_4$]$^-$ or [L]$^+$[Z(A)$_4$]$^-$      [Formula 6]

in the above formula, L is a neutral or a cationic Lewis acid; H is a hydrogen atom; Z is an element in group 13; each A is independently aryl having 6 to 20 carbon atoms or alkyl having 1 to 20 carbon atoms, where at least one hydrogen atom are optionally and independently be substituted with a substituent; and the substituent is halogen, hydrocarbyl having 1 to 20 carbon atoms, alkoxy having 1 to 20 carbon atoms or aryloxy having 6 to 20 carbon atoms.

11. The catalyst composition of claim 8, further comprising a reaction solvent.

12. A preparation method of an olefin polymer comprising performing a polymerization reaction in the presence of the catalyst composition described in claim 8.

13. The preparation method of an olefin polymer of claim 12, wherein the polymer is a homopolymer or a copolymer of polyolefin.

* * * * *